United States Patent [19]

Milks

[11] Patent Number: 5,198,467

[45] Date of Patent: Mar. 30, 1993

[54] INSECTICIDE FOR IMPORTED FIRE ANTS AND OTHER INSECT PESTS

[76] Inventor: Robert R. Milks, 1805 Oregon St., Baton Rouge, La. 70802

[21] Appl. No.: 558,753

[22] Filed: Jul. 27, 1990

Related U.S. Application Data

[63] Continuation-in-part of Ser. No. 142,525, Jan. 11, 1988, abandoned.

[51] Int. Cl.⁵ ............................................ A01N 41/04
[52] U.S. Cl. ................................... 514/553; 514/578
[58] Field of Search ............... 514/553, 578; 424/410, 424/1; 426/1; 562/30, 113

[56] References Cited

U.S. PATENT DOCUMENTS

| | | | |
|---|---|---|---|
| 3,220,921 | 11/1965 | Greenbaum et al. | 514/755 |
| 3,925,297 | 12/1975 | Sprengling | 523/200 |
| 4,092,110 | 5/1978 | Adolphi et al. | 21/7 |
| 4,921,696 | 5/1990 | Vander Meer et al. | 424/84 |

OTHER PUBLICATIONS

*CAS Registry Handbook*, 1985 Supplement, p. 2370RN (1985).
*CAS Registry Handbook*, 1965–1971, p. 1696R (1971).
Moot et al., *Chem. Abs.* 94(10): 67225m (1981).
Frisch et al., *Chem. Abs.* 94(10): 75634j (1981).
Umemura et al., *Chem. Abs.* 87(18): 128902j (1977).
Karasawa et al., *Chem. Abs.* 85(12): 798311 (1976).
"Laboratory and Field Evaluation of Several Organochlorine and Organophosphorus Compounds for Control of Imported Fire Ants," Agricultural Research Service, U.S. Department of Agriculture, ARS-S-169, Oct., 1977, pp. 2–3.
Hamman, P. J., "Fire Ants and Their Control," Texas Agricultural Extension Service Publication L-2034, The Texas A&M University System, College Station, Tex. (1987).
Vander Meer, R. K., Lofgren, C. S., and Williams, D. W., "Fluoroaliphatic Sulfones: A New Class of Delayed-Action Insecticides for Control of Solenopsis invicta (Hymenoptera: Formicidae)," Journal of Economic Entomology, vol. 78, No. 6, Dec., 1985, pp. 1190–1197.
Vander Meer, R. K., Chemical Abstracts, vol. 100, No. 1, 2205c, Jan. 2, 1984, p. 193.

*Primary Examiner*—Carolyn Elmore
*Assistant Examiner*—Scott C. Rand
*Attorney, Agent, or Firm*—William C. Milks, III

[57] ABSTRACT

An effective delayed-action insecticide for use against the imported fire ant (IFA), as well as against infestations of other insects. The insecticide consists of an oil insoluble surfactant, preferably an anionic fluorochemical surfactant, as the active ingredient. The insecticide further consists of a carrier, which is a source of food for the IFA or other insect. This carrier is impregnated with the anionic fluorosurfactant to provide a toxic bait. In a preferred embodiment, the insecticide contains 0.3 to 0.5% by weight anionic fluorosurfactant; and a member selected from the group comprising dried yellow corn meal, corn grit, crushed wheat, and cracked wheat in a concentration of 94.7 to 94.5% by weight, as the carrier. Soybean oil, in a concentration of 5.0% by weight, is preferably applied as an attractant. A method for formulating the insecticide by dissolving the anionic fluorosurfactant in a solvent, such as acetone or methanol, and mixing the resulting solution with the carrier, is also disclosed. Formulations consist of the active ingredient (anionic fluorosurfactant) dissolved in the solvent and then absorbed onto the carrier, soybean oil then preferably being added as an attractant.

13 Claims, 2 Drawing Sheets

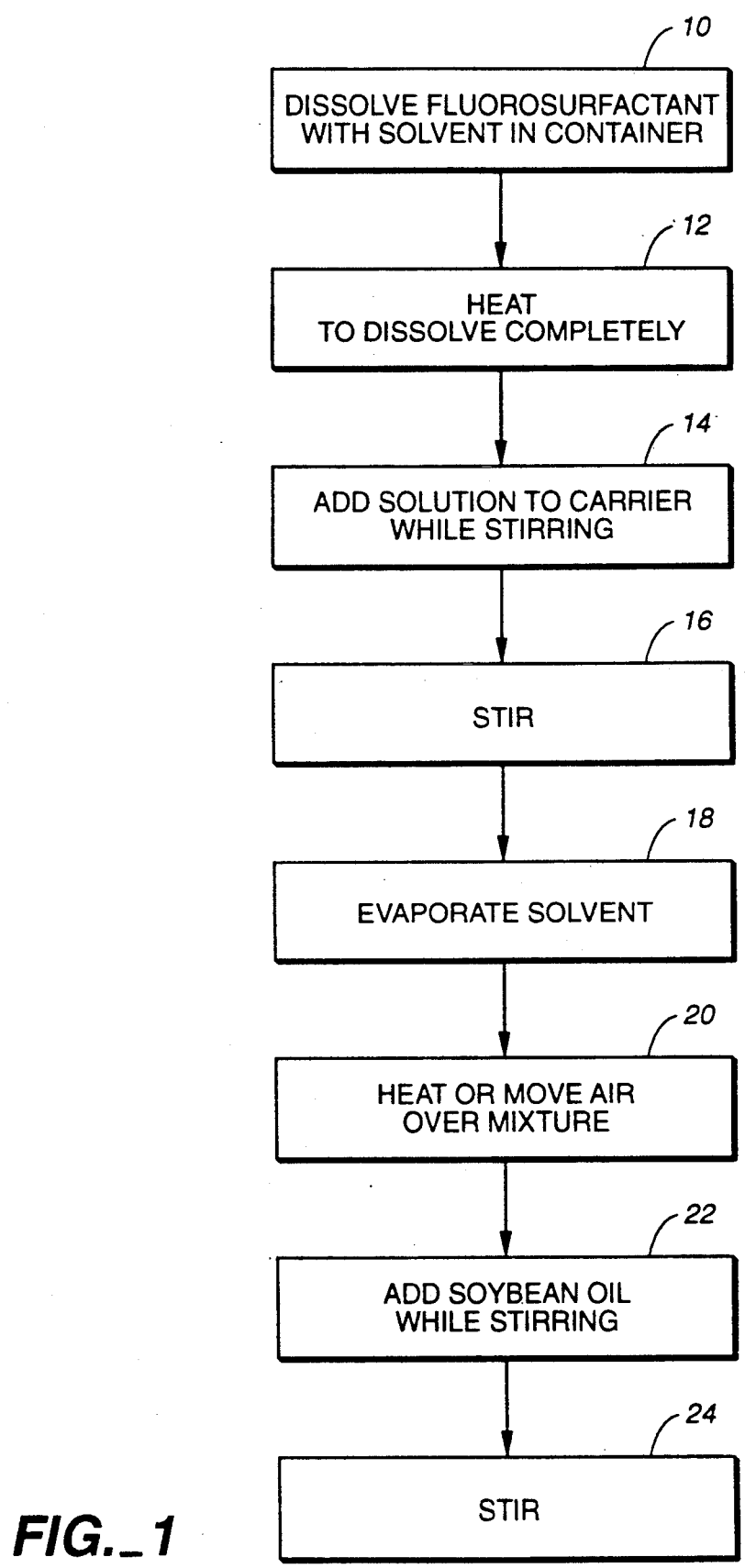
FIG._1

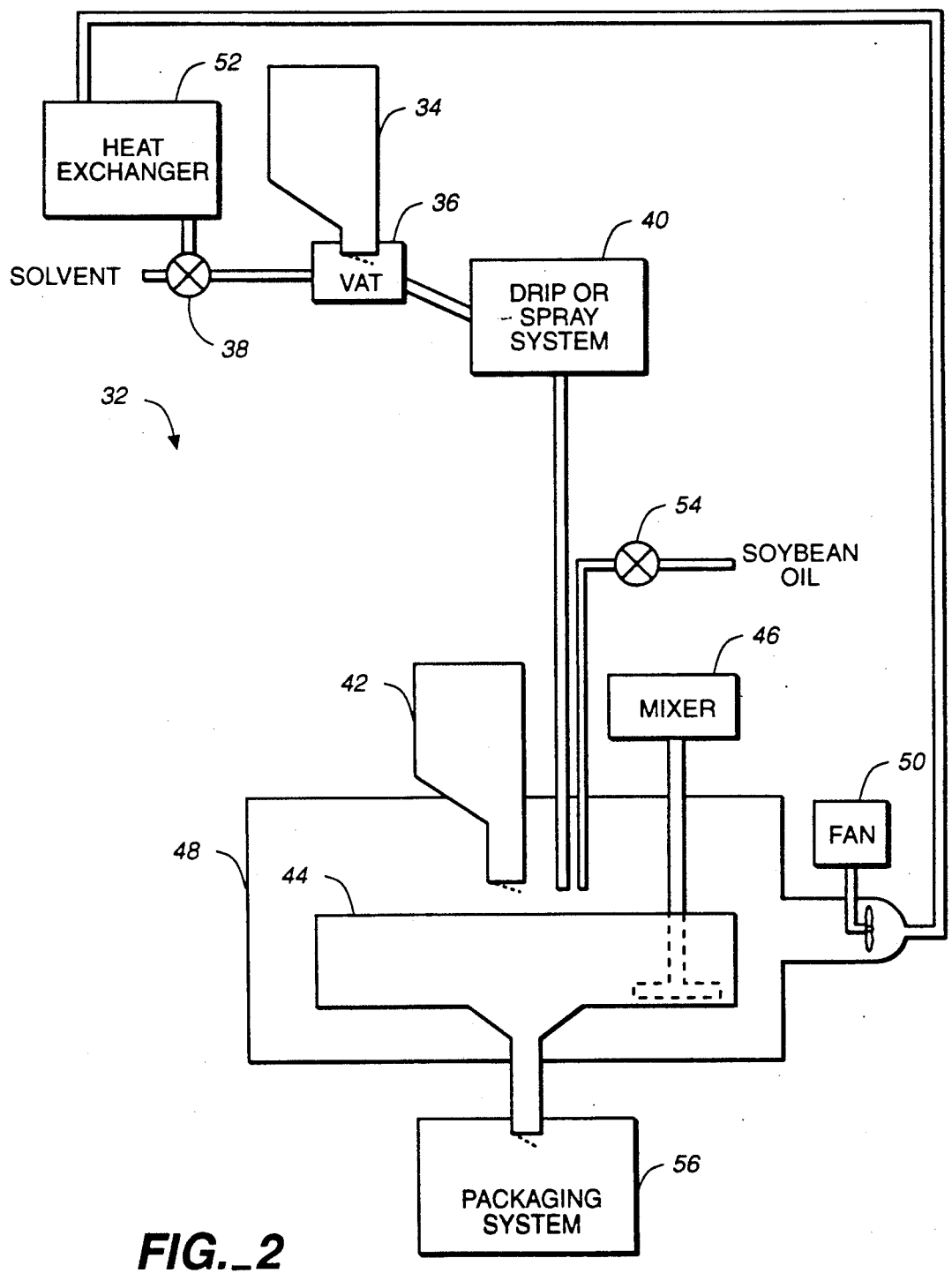
FIG._2

INSECTICIDE FOR IMPORTED FIRE ANTS AND OTHER INSECT PESTS

CROSS-REFERENCE TO RELATED APPLICATIONS

This patent application is a continuation-in-part of U.S. patent application Series Code/Ser. No. 07/142,525, entitled "Imported Fire Ant Insecticide," filed on Jan. 11, 1988, in the name of Robert R. Milks, now abandoned.

BACKGROUND OF THE INVENTION

This invention relates to poisons and, more particularly, to a poison in the form of a delayed-action insecticide, as opposed to an insecticide in the form of a contact poison, to eradicate an infestation of insects. Specifically, one embodiment of the invention is directed to an effective delayed-action insecticide to destroy the imported fire ant (IFA).

The IFA menace is a real and serious problem. Since accidental introduction of the black imported fire ant at the port of Mobile, Ala. in 1918, and its cousin the red imported fire ant in 1940, also at the port of Mobile, Ala., the IFA has spread rapidly. Its domain now ranges from Mexico to the Atlantic Coast states of the United States.

Imported fire ants damage young plants by gnawing holes in roots, tubers, stalks, and buds. They can attack young, unprotected animals, such as newborn calves and pigs and newly hatched poultry, as well as field workers in rural areas. They infest homes and businesses in urban areas as well. Their stings are painful and pose a threat to health. Venom of the IFA is unlike that of other stinging insects. Some persons are hypersensitive to this venom and can suffer chest pains or nausea and even lapse into a coma from one sting. Mounds damage machinery, hinder mowing operations, and reduce land value in heavily infested regions.

Previously, various materials have been utilized to fight the IFA, such as used oil, gasoline, detergents (laundry products), and large amounts of pesticides. Typically, these materials pollute and harm the environment.

Currently, there is a number of commercial products in the form of pesticides, which are utilized against the IFA. See Philip J. Hamman, "Fire Ants and Their Control," Texas Agricultural Extension Service Publication L-2034, The Texas A&M University System, College Station, Tex., which includes a partial list of products registered as IFA pesticides. These pesticides are typically contact poisons and are effective in killing a wide variety of insects.

Another class of materials occasionally utilized comprises solvents, such as methylene chloride. These solvents are also contact poisons.

All of the above materials have drawbacks. They kill only on contact, and therefore do not kill the queen which is far underground. The result is that one or more new mounds develop a short distance away from the treated site.

Another commercial product, which is specifically targeted at the IFA, is AMDRO (registered trademark of American Cyanamid Company). This product is a delayed-action pesticide advertised to be very effective against the IFA, because it is eventually ingested by the queen. When the queen is killed, the colony vanishes as the current generation ages and dies. Therefore, unlike the earlier mentioned materials, AMDRO can destroy the mound. However, while AMDRO can destroy the mound, it too has a number of drawbacks.

AMDRO loses efficacy following contact with rain or humidity. This is a serious shortcoming, since the IFA domain is primarily along the southern coast of the United States where rainfall is plentiful. Furthermore, the active ingredient in AMDRO is readily degradable, and therefore its shelf life after its container is opened is very short. The manufacturer recommends that the supply of AMDRO be exhausted within a three-day period after opening the bag. Not surprisingly, its effectiveness in the field is also very short. Finally, AMDRO is expensive, and like other expensive pesticides, it cannot be broadcast over large areas economically. The expense of AMDRO also discourages repeat applications. Accordingly, the contact poisons mentioned above, although not as effective as AMDRO under ideal conditions, are more generally utilized.

Another class of materials investigated as potential IFA toxicants is mentioned in R.K. Vander Meer, C.S. Lofgren, and D.W. Williams, "Fluoroaliphatic Sulfones: A New Class of Delayed-action Insecticides for Control of *Solenopsis invicta* (Hymenoptera: Formicidae)," *Journal of Economic Entomology*, Vol. 78, No. 6, December, 1985, pp. 1190-1197. Importantly, this article states in the left hand column on page 1196:

"Large-scale RIFA [red imported fire ant] control is most effectively done with toxicants formulated in baits. Formulations consist of the toxicant dissolved in soybean oil and then absorbed onto a suitable carrier (i.e., corn grits, pregel defatted corn grits). Solid suspensions are not suitable because the RIFA workers have a sophisticated and efficient mechanism for filtering submicron particles from ingested food [Citation omitted.] Consequently, oil solubility is an essential property for any potential RIFA toxicant."

Although the article primarily describes fluoroaliphatic sulfones as IFA toxicants, Table 9 of this article, appearing on page 1196, shows test data for various sulfonic acids and sulfonate salts. These materials were formulated at 1.0% concentrations in honey/water (1:1) and tested against the red imported fire ant. Table 9 lists $C_8F_{17}SO_3K$, otherwise known as FC-95 available from 3M Company, St. Paul, Minn., which is a sulfonate salt. FC-95 is totally insoluble in vegetable oils, such as soybean oil. Accordingly, this article concludes in the right hand column on page 1196 that "the solubility properties of the compounds listed in Table 9," including FC-95, "make them poor candidates for RIFA control." It is therefore desirable to formulate a delayed-action insecticide based on materials, such as these sulfonic acids and sulfonate salts, which are not soluble in vegetable oil, for use against the IFA, as well as other insects.

SUMMARY OF THE INVENTION

The present invention provides an effective delayed-action insecticide for use against the imported fire ant (IFA), as well as against other infestations of insects, the insecticide consisting of a surfactant, preferably an anionic fluorochemical surfactant (fluorosurfactant), as the active ingredient. The anionic fluorosurfactant is insoluble in vegetable oil. The insecticide further consists of a carrier, which is a source of food for the IFA or other insect. This carrier is impregnated with the anionic fluorosurfactant to provide a toxic bait.

In a preferred embodiment, the insecticide contains 0.3 to 0.5% by weight anionic fluorosurfactant; and a member selected from the group comprising dried yellow corn meal, corn grit, crushed wheat, and cracked wheat in a concentration of 94.7 to 94.5% by weight, as the carrier. Soybean oil, in a concentration of 5.0% by weight, is preferably applied as an attractant.

The invention also provides a method for producing the insecticide by dissolving the anionic fluorosurfactant in a solvent, such as acetone or methanol, and mixing the resulting solution with the carrier. Preferably, the insecticide is prepared in a closed system, and the solvent is recovered upon evaporation and recycled. Formulations consist of the active ingredient (anionic fluorosurfactant) dissolved in the solvent and then absorbed onto the carrier, soybean oil then preferably being added as an attractant.

Importantly, although the IFA workers have a sophisticated and efficient mechanism for filtering submicron particles from ingested food, the insecticide in accordance with the invention is absorbed onto the carrier in such a way that the bait is not effectively filtered by the ants. Also, the insecticide of the invention has a long shelf life and toxicity following broadcast, and is not rendered ineffective upon contact with water or humidity. The insecticide has demonstrated efficacy against the IFA and can be produced economically.

BRIEF DESCRIPTION OF THE DRAWINGS

The above and other features of the delayed-action insecticide, and process for making the insecticide, in accordance with the invention. and the concomitant advantages, will be better appreciated by persons skilled in the art in view of the description given below in conjunction with the accompanying drawings. In the drawings:

FIG. 1 is a flow diagram of the method for making the delayed-action insecticide in accordance with the invention; and FIG. 2 is a block diagram of a delayed-action insecticide production system of the invention.

DETAILED DESCRIPTION OF THE PREFERRED EMBODIMENTS

The present invention provides a delayed-action insecticide particularly effective against the imported fire ant (IFA). The active ingredient of the insecticide is selected from a class of materials known as surfactants.

Surfactants are powerful chemicals which are capable of reducing the surface tension of a liquid at relatively low concentrations. Surfactants act at surfaces to change the chemical nature of the surface. Since many biological systems function at surfaces (transport at membranes, etc.), a surfactant can disrupt one of these biological systems by changing the surface where the biological process takes place.

Generally, surfactants consist of an organic compound having an insoluble moiety (which is inherently insoluble in the liquid in which it is useful) combined with a solubilizing group. Surfactants can be divided into three major chemical classes, hydrocarbons, silicones, and fluorochemicals. This classification describes the "tail" portion of the surfactant molecule. A fluorochemical surfactant, or fluorosurfactant, for example, has a stable fluorocarbon tail.

In order for the surfactant to be effective as an insecticide, it has been found that the surfactant should not be utilized as a contact poison, but rather as the active ingredient in a delayed-action poison preferably formulated in a bait intended to be eaten by the IFA or other insect. In view of the social nature of the IFA, worker ants gather the tainted food (bait) and feed it to the queen(s) so that the queen is also exposed to the surfactant. Accordingly, various additional important criteria must be met.

First, the surfactant must be stable under acidic conditions. This is because some bait is initially ingested by workers and later regurgitated to other members of the colony to feed them; and the digestive system of insects, such as the IFA, is highly acidic.

Second, some insects, and the IFA in particular, are difficult to control because fast-acting toxicants formulated in baits affect only a small percentage of foraging workers with little effect on the total colony. In addition, the foraging workers pass ingested toxicants to other members of the colony, thus diluting the effects of the toxicant. Delayed toxicity over a range of concentrations is therefore needed.

As a corollary to this criterion, the surfactant should not be used in concentrations high enough to disable the IFA or other insect which transports the tainted bait to the remainder of the colony. In the case of the IFA, for example, the bait is taken by the foraging workers into the mound where the ants, including queens and brood, feed on it. The adult workers, which ingest food and regurgitate it to help feed the queen(s) and brood, are eventually killed directly by the surfactant. Therefore, the effect of the surfactant on the IFA must be slow-acting so that any tainted bait does not immediately impair the workers. That is, in order to kill the queen IFA, the surfactant carried or initially ingested by the foraging members of the colony must be transferred to the queen(s) and any other immature queen among the brood (i.e., fed or regurgitated to her by the foraging ants). If the foraging ants are disabled or die prematurely, the surfactant will not be fed to the queen(s), and she will not be killed.

Third, the surfactant must be effective when exposed to water, such as rain, or water vapor (humidity). It is also desirable that the surfactant is not soluble or has very low water solubility in order that dilution effects are avoided, as well as to minimize the widespread distribution of the surfactant into the surrounding environment. Also, the surfactant should be chemically inert (i.e., not chemically reactive) so that it retains its chemical characteristics and thus its toxicity.

Fourth, the surfactant must be toxic to the intended victim (i.e., the IFA or other insect). However, since any IFA insecticide is likely toxic to other life forms if ingested in sufficient quantities, it is desirable that the effective dose for the IFA not be a substantial threat to other living things, such as birds and other wildlife.

Fifth, the surfactant is desirably effective at low concentrations, both for economic reasons and also for environmental reasons.

In view of these criteria, preferably, a fluorochemical surfactant (fluorosurfactant), for example, a FLUORAD (registered trademark of 3M) brand anionic fluorosurfactant, such as FC-95, 3M I.D. Number 98-0207-0103-7, for example, or FC-98, 3M I.D. Number 98-0207-0203-5, for example, in concentrations ranging from 0.05 to 1.0% with a preferred range of 0.3 to 0.5% by weight, is the active ingredient of the delayed-action insecticide in accordance with the invention. FC-95 can be generally described as a potassium perfluoroalkyl sulfonate, $C_nF_{2n+1}SO_3K$, where n preferably equals 6 or 8. FC-98 can be generally described as a potassium perfluoroalkyl cyclohexyl sulfonate, $C_nF_{2n-1}SO_3K$, where n preferably equals 7 or 8. Both FC-95 and FC-98 characteristically exhibit low solubility in water and most inorganic solvents. Both FC-95 and FC-98 contain an $SO_3^-$ (sulphonate group) functionality, which has been found to contribute significantly to toxic efficacy against the IFA. At the preferred concentrations, the resulting insecticide is very effective in destroying IFA colonies.

The delayed-action insecticide of the invention is formulated as follows. Referring to FIG. 1, a predetermined amount of fluorosurfactant, for example, . FC-95 or FC-98 anionic fluorosurfactant, is dissolved in a solvent, as indicated by the numeral 10. The solvent preferably consists of a member selected from the group comprising acetone and methanol. Heat can be applied to dissolve the fluorosurfactant completely, as indicated by the numeral 12.

As indicated by the numeral 14, the fluorosurfactant/solvent solution is added to a carrier consisting of a member selected from the group comprising dried yellow corn meal, corn grit, crushed wheat, and cracked wheat, so that all of the carrier is moistened. The fluorosurfactant/solvent solution and carrier mixture is preferably stirred as the solution is added, as indicated by the step 14, so that the solution is properly dispersed throughout the carrier. The mixture is stirred thoroughly so that the solution is evenly distributed throughout the mixture, as indicated by the step 14 and the numeral 16.

The solvent can be allowed to evaporate from the carrier, as indicated by the numeral 18. Heat can also be applied, or air forced over the mixture, to assure that the solvent is completely evaporated, as indicated by the numeral 20.

Finally, soybean oil is added to the mixture as an attractant, as indicated by the numeral 22. The mixture is stirred thoroughly to disperse the soybean oil throughout the mixture, as indicated by the step 22 and the numeral 24.

The preferred concentrations are 0.3 to 0.5% anionic fluorosurfactant, 94.7 to 94.5% carrier, and 5.0% soybean oil, by weight. Concentrations of 0.05 to 1.0% anionic fluorosurfactant (94.95 to 94.0% carrier) and 5.0% soybean oil by weight, also have demonstrated efficacy. Several specific bait formulations of the anionic fluorosurfactant insecticide will now be described.

EXAMPLE 1

1.0%: 3.05 grams of FC-95 anionic fluorosurfactant are dissolved in 50 grams of acetone. Heat can be applied to dissolve the anionic fluorosurfactant completely.

The fluorosurfactant/acetone solution is added to 287 grams of a carrier consisting of dried yellow corn meal and mixed thoroughly, moistening all of the corn meal. The container used to form the solution is rinsed with a small additional amount of acetone, and this liquid is also added to the mixture, thereby assuring that all of the anionic fluorosurfactant is utilized. The mixture is stirred thoroughly so that the solution is evenly distributed throughout the mixture.

The acetone can be allowed to evaporate from the corn meal. In this example, the acetone evaporated in approximately two hours. Heat can also be applied to assure that the acetone is completely evaporated from the mixture. In this example, the mixture is placed in a 170 degree F oven for 45 minutes. The mixture is then removed from the oven and allowed to sit for 24 hours.

Finally, approximately 12 grams of soybean oil is added to the mixture as an attractant. The mixture is again stirred thoroughly to disperse the soybean oil throughout the mixture.

The above anionic fluorosurfactant insecticide bait formulation was tested in the side yard on the west side of a residence located in the vicinity of Angleton, Tex. containing thirteen IFA mounds. The procedure for treating the mounds was to lightly sprinkle the above formulation around the perimeter of the mound. In light of the small amount of insecticide being tested, the anionic fluorosurfactant insecticide had to be used sparingly around the base of each mound. The IFA began to forage the insecticide immediately.

The test site was inspected 24 days later. There was no evidence of IFA activity at eleven of the thirteen mounds (i.e., eleven mounds were dead). The largest of the mounds that was tested, as well as one other nest, were noted to have developed mounds on the fringe of the former mounds.

EXAMPLE 2

0.1%: An insecticide formulation of 0.1% anionic fluorosurfactant contains 0.3 gram of FC-95 anionic fluorosurfactant dissolved in approximately 50 grams of acetone and applied to 289.7 grams of dried yellow corn meal according to the procedure described in Example 1 above. Approximately 12 grams of soybean oil is added to the anionic fluorosurfactant impregnated corn meal after evaporating the acetone and allowing the mixture to sit.

The rear mounds in the side yard of the Angleton, Tex. residence were treated with the Example 2 insecticide bait formulation (0.1% anionic fluorosurfactant) by lightly sprinkling the insecticide around the perimeter of each of the mounds. This area contained seven IFA mounds that were totally treated, as well as an eighth mound that was partially treated with the remaining insecticide. The IFA again began to forage the insecticide immediately.

These mounds were inspected 24 days after the insecticide (0.1% anionic fluorosurfactant) was distributed. Three of the eight mounds tested were dead. There was evidence of developing mounds on the fringes of the other five nests.

EXAMPLE 3

0.5%: A large batch of anionic fluorosurfactant insecticide having a concentration of 0.5% active ingredient can be prepared by dissolving 5.0 grams of FC-95 anionic fluorosurfactant in approximately 200 grams of acetone (including rinse), which is then added to approximately 955 plus or minus 10 grams of dried yellow corn meal according to the procedure described in connection with Example 1 above. It is preferable to add the fluorosurfactant/acetone solution to the corn meal while stirring the corn meal to better distribute the active ingredient throughout the corn meal, when a large amount (i.e., one kilogram or more) of insecticide is being prepared. Approximately 40 plus or minus 5 grams of soybean oil is added to the mixture after evaporating the acetone and allowing the mixture to sit.

The 0.5% anionic fluorosurfactant insecticide bait formulation was tested at the Angleton, Tex. residence in the front, north side, and back yards, as well as the driveway area. The insecticide was lightly sprinkled around the perimeter of fifty-four mounds. The insecticide was applied on the day following heavy spring rainfall. The test sites were inspected 25 days following insecticide application. Fifty-two of the fifty-four mounds were dead. The remaining two mounds evidenced reduced IFA populations, with new nests just beginning to develop near these two.

EXAMPLE 4

R.K. Vander Meer, C.S. Lofgren, and D.W. Williams, "Fluoroaliphatic Sulfones: A New Class of Delayed-action Insecticides for Control of *Solenopsis invicta* (Hymenoptera: Formicidae)," *Journal of Economic Entomology*, Vol. 78, No. 6, December, 1985, pp. 1190–1197, states in the left hand column on page 1196 that "[l]arge-scale RIFA [red imported fire ant] control is most effectively done with toxicants formulated in baits . . ." and that "oil solubility is an essential property for any potential RIFA toxicant." Therefore, the article concludes in the right hand column on page 1196 that "the solubility properties of the compounds listed in Table 9," including FC-95 anionic fluorosurfactant, which is totally insoluble in vegetable oils, such as soybean oil, "make them poor candidates for RIFA control." Rather than formulate a bait, the article indicates that FC-95 anionic fluorosurfactant was formulated at a 1.0% concentration in honey/water (1:1) and tested against the red imported fire ant.

Contrary to the teaching of the article that only toxicants soluble in vegetable oils are suitable for bait formulations, a 1.0% FC-95 anionic fluorosurfactant bait formulation was prepared. In an effort to evaluate the efficacy of this bait formulation, it was tested along with a 1.0% concentration FC-95 anionic fluorosurfactant in honey/water (1:1) against the red imported fire ant.

Specifically, side-by-side evaluations of a 1.0% FC-95 anionic fluorosurfactant bait formulation and a 1.0% concentration of FC-95 anionic fluorosurfactant formulated in honey/water (1:1) were conducted against whole red imported fire ant colonies. Except for the size of the bioassay (entire red imported fire ant colonies versus twenty worker ants) and the test environment (field test versus laboratory test), the evaluations were performed in a manner consistent with the study reported in the article.

In view of certain probabilistic variables, including the fact that the activity of red imported fire ants is not always predictable and the fact that the evaluation was to be conducted in a natural setting where heavy rain is possible, two identical tests were conducted. The results of these two tests were then combined.

A 1.0% FC-95 anionic fluorosurfactant bait formulation (1.0% FC-95 anionic fluorosurfactant, 95.0% dried yellow corn meal, and 4.0% soybean oil) was prepared according to the procedure described in Example 1 above. Initially, 2.0 grams of FC-95 anionic fluorosurfactant is dissolved in acetone. The fluorosurfactant/acetone solution is next added, with thorough mixing, to 190.0 grams of dried yellow corn meal. The acetone is then evaporated from the corn meal. Finally, 8.0 grams of soybean oil is mixed into the anionic fluorosurfactant impregnated corn meal.

A 1.0% liquid formulation of FC-95 anionic fluorosurfactant (1.0% FC-95 anionic fluorosurfactant in honey/water solution) was then prepared as described in the article. Initially, 99.0 grams of water is added to 99.0 grams of honey to produce a 1:1 honey/water solution. Then, 2.0 grams of FC-95 anionic fluorosurfactant is added to the 1:1 honey/water solution.

Additionally, two controls were prepared. The first control was a bait formulation. The bait control consists of 96.0% dried yellow corn meal and 4.0% soybean oil. It is prepared by simply adding 8.0 grams of soybean oil to 192.0 grams of dried yellow corn meal with thorough mixing. The liquid control consists of a 1:1 honey/water solution. It is prepared by mixing 100.0 grams of honey and 100.0 grams of water.

After the test materials were prepared, a suitable test site near a residence in Baton Rouge, La. was selected. Active red imported fire ant mounds were treated with the test materials in the morning, while the ants were observed to be foraging.

In each of the two tests, three red imported fire ant mounds were treated with the FC-95 anionic fluorosurfactant bait formulation, and three mounds were treated with the FC-95 anionic fluorosurfactant in 1:1 honey/water solution. Also, the corn meal/soybean oil control was deployed at one mound, and the honey/water control was deployed at another mound.

At red imported fire ant mounds treated with the FC-95 anionic fluorosurfactant bait formulation, the bait was poured on a piece of polyethylene positioned at each of two specific locations at the perimeter of each of the three mounds treated. Similarly, the corn meal/soybean oil control was placed on a piece of polyethylene at each of two corresponding locations at the perimeter of a fourth red imported fire ant mound. Red imported fire ants were observed to immediately begin to forage both the FC-95 anionic fluorosurfactant bait formulation and the corn meal/soybean oil control.

The FC-95 anionic fluorosurfactant in 1:1 honey/water solution was placed in small glass bottles and then plugged with medicinal cotton to serve as a wick. The cotton was allowed to become moist before the bottles were deployed. Two bottles of FC-95 anionic fluorosurfactant in 1:1 honey/water solution were placed at the perimeter of each of three red imported fire ant mounds in locations corresponding to the locations of the pieces of polyethylene containing the FC-95 anionic fluorosurfactant bait formulation around the mounds treated with the bait formulation. Also, two cotton plugged bottles with the honey/water control were positioned at the perimeter of yet another red imported fire ant mound in corresponding locations. Red imported fire ants were also observed to immediately contact the moistened cotton.

A duplicate test with fresh test materials and controls, prepared as described above, was begun four days after the first test commenced. All remaining test materials were retrieved twenty-four hours after deployment, so that the time that the red imported fire ants were exposed to the test materials was the same. The tests were terminated 21 days after the test materials were deployed.

Three days after the first test began, substantial numbers of dead red imported fire ants appeared at two of the mounds treated with the FC-95 anionic fluorosurfactant bait formulation. The other mound appeared to have been abandoned, since no ant activity or dead ants were observed. However, a substantial number of dead ants appeared at the mound where the corn meal/soybean oil control was deployed, which was located at a ten to fifteen foot distance from the abandoned mound treated with the FC-95 anionic fluorosurfactant bait formulation. It was therefore concluded that the abandoned mound and the mound at which the corn meal/soybean oil control was deployed were both inhabited by the same red imported fire ant colony.

Conversely, only a few dead red imported fire ants were observed after three days at two of the three red imported fire ant mounds treated with FC-95 anionic fluorosurfactant in 1:1 honey/water solution. No dead red imported fire ants and minimal ant activity were observed at the remaining mound treated with FC-95 anionic fluorosurfactant in 1:1 honey/water solution, and, therefore, this mound was considered to have been abandoned. The ant activity at the mound where the honey/water control was deployed appeared normal, and there was no sign of ant mortality.

Six days after the beginning of the first test, ant mortality increased at the two non-abandoned mounds treated with the FC-95 anionic fluorosurfactant bait formulation and at the mound where the corn meal/soybean oil control was deployed. No additional ant mortality was observed at the two non-abandoned mounds treated with FC-95 anionic fluorosurfactant in 1:1 honey/water solution, and ant activity continued to appear normal at the mound where the honey/water control was deployed. By way of comparison, the ant mortality at one mound treated with the FC-95 anionic fluorosurfactant bait formulation was estimated to be tenfold the ant mortality at all mounds treated with FC-95 anionic fluorosurfactant in 1:1 honey/water solution combined.

At the conclusion of the first test (21 days), two of the red imported fire ant mounds treated with the FC-95 anionic fluorosurfactant bait formulation were dead (no ant activity), the abandoned mound treated with the FC-95 anionic fluorosurfactant bait formulation evidenced no ant activity, and the mound where the corn meal/soybean oil control was deployed was dead. In contrast, two mounds treated with FC-95 anionic fluorosurfactant in 1:1 honey/water solution were active and thriving, the abandoned mound treated with FC-95 anionic fluorosurfactant in 1:1 honey/water solution showed some ant activity, and the mound at which the honey/water control was deployed was active and approximately the same size as when the test began.

Observations and results of the second test were as follows. After 21 days (at the conclusion of the second test), all three mounds treated with the FC-95 anionic fluorosurfactant bait formulation were dead. Additionally, a large red imported fire ant mound in the vicinity of one of the mounds treated with the FC-95 anionic fluorosurfactant bait formulation evidenced substantial ant mortality and appeared to be dying. Unlike the first test, the mound where the corn meal/soybean oil control was deployed was thriving and appeared to have grown.

In contrast, at the conclusion of the second test (after 21 days), one red imported fire ant mound treated with FC-95 anionic fluorosurfactant in 1:1 honey/water solution appeared to be thriving, while a second mound appeared to show reduced ant activity, but was still active. The third mound treated with FC-95 anionic fluorosurfactant in 1:1 honey/water solution was abandoned (this mound was active until the sixteenth day of the second test when heavy rain occurred). The mound at which the honey/water control was deployed was also abandoned (this mound was also active until the sixteenth day of the test when the heavy rain occurred), and it appeared that the ant colony had established a new mound approximately seven feet away.

In summary, the tests described above evidence that the FC-95 anionic fluorosurfactant bait formulation was extremely effective (five of six treated red imported fire ant mounds killed, the sixth mound being abandoned, as well as two untreated mounds killed). This performance was observed in spite of the undesirable manner in which the mounds were treated (FC-95 anionic fluorosurfactant bait formulations are more effective when sprinkled around the perimeter of the mounds and when deployed for longer than twenty-four hours, as described in the examples above). In contrast, FC-95 anionic fluorosurfactant in 1:1 honey/water solution prepared as described in the article was ineffective (zero mounds killed and minimal ant mortality observed).

Although the anionic fluorosurfactant insecticide bait formulations described above have demonstrated effectiveness against the IFA, the active ingredient (FC-95) is considered only moderately toxic to mammals upon ingestion. The $LD_{50}$ (rat, acute oral) is 251 mg/kg for FC-95.

EXAMPLE 5

1.0%: 40 grams of a 15.0% (by weight) acetone, 85.0% (by weight) distilled water solution is prepared. Next, 2.0 grams of FC-98 anionic fluorosurfactant is dissolved in the acetone/water solution. The fluorosurfactant/acetone/water solution is then added to 178.0 grams of a carrier consisting of dried yellow corn meal and mixed thoroughly, moistening all corn meal with the fluorosurfactant/acetone/water solution. The mixture is thereafter placed in an oven at a temperature of 150 degrees F for ten hours to evaporate the acetone and water. Thorough evaporation of the water is desirable to prevent spoilage of the corn meal. Finally, 20 grams of soybean oil is added to the dried anionic fluorosurfactant impregnated corn meal as an attractant and thoroughly stirred to disperse the soybean oil throughout the mixture.

The FC-98 anionic fluorosurfactant insecticide bait formulation was tested in the yard on the south side of a residence located in Baton Rouge, La. having six IFA mounds. The procedure for treating the mounds with the FC-98 anionic fluorosurfactant insecticide was to lightly sprinkle the insecticide around the perimeter of each mound, as described in Examples 1-3 above. IFA began to forage the FC-98 anionic fluorosurfactant insecticide immediately.

The side yard was periodically inspected over the course of the following seven days. Substantial ant mortality was observed within forty-eight hours after the FC-98 anionic fluorosurfactant insecticide was deployed. Ant mortality was observed to increase during the following several days. By the seventh day, ant activity at the treated mounds had virtually ceased.

In general, the utilization of FC-95 anionic fluorosurfactant is preferred to the use of FC-98 anionic fluorosurfactant in formulating baits. The reason is that the solubility of FC-98 anionic fluorosurfactant is improved when an acetone/water solution is utilized, but care must be exercised when water is used to prevent spoilage of the carrier. Also, reclaiming acetone is complicated by the presence of water, and a water treatment system is needed. These factors add to the cost of a commercial scale bait formulation process.

Although the FC-98 anionic fluorosurfactant insecticide bait formulation described above has demonstrated effectiveness against the IFA, the active ingredient (FC-98) is considered only moderately toxic to mammals upon ingestion. The $LD_{50}$ (rat, acute oral) is between 1.25 and 2.5 g/kg for FC-98.

FIG. 2 shows a block diagram of a delayed-action insecticide production system in accordance with the invention, generally indicated by the numeral 32. The system 32 comprises a fluorosurfactant hopper 34 for metering fluorosurfactant into a vat 36. Solvent is initially fed through a solvent valve 38 into the vat 36 where the fluorosurfactant/solvent solution is formed.

The fluorosurfactant/solvent solution is preferably fed to a drip or spray system 40 which adds the solution to carrier material metered from a carrier hopper 42 into a mixing trough 44. A mixer 46, such as a Hobart mixer, stirs the fluorosurfactant/solvent solution and carrier as the solution is added to the mixture. After the appropriate amount of fluorosurfactant/solvent solution is added, the drip or spray system 40 is deactivated.

The mixer 46 continues to stir the mixture until the carrier is thoroughly moistened with the fluorosurfactant/solvent solution, and then the mixer is deactivated. Next, the solvent is evaporated from the mixture. Preferably, the mixing trough 44 is contained in a solvent recovery chamber 48, and a vacuum system 50 is connected to the solvent recovery chamber for enhancing evaporation of the solvent. Alternatively, a forced air evaporation system can be substituted for the vacuum system 50. Evaporated solvent is channeled through a heat exchanger (refrigeration coils) 52 and fed through the solvent valve 38 to the vat 36, thereby recycling the solvent.

After the solvent is evaporated, soybean oil is added to the dried mixture through a soybean oil valve 54 and stirred by the mixer 46 to disperse the soybean oil. The insecticide is then conveyed to a packaging system 56.

Several bait formulations of the delayed-action anionic fluorosurfactant insecticide in accordance with the invention, as well as methods for formulating them, have been described by way of example. Alternatively, the solvent can comprise methanol or another appropriate solvent. The carrier can comprise corn grit, crushed wheat, cracked wheat, or other grain, or another suitable material which is an edible food for insects. Various other modifications will occur to persons skilled in the art without departing from the spirit of the invention. Furthermore, although the insecticide of the invention has been specifically tested against the imported fire ant, the insecticide can be utilized as an insecticide against other ants and other insects, such as American and German cockroaches and other roaches and termites. In the case of termites, the carrier can consist of cellulose, which is impregnated with anionic fluorosurfactant. Accordingly, the scope of the invention can only be ascertained by reference to the appended claims.

What is claimed is:

1. A delayed-action insecticide comprising an insecticidal vegetable oil insoluble anionic fluorochemical surfactant, the surfactant being applied in an insecticidal concentration in solution to a carrier in the form of dispersible nonliquid edible food to form a toxic bait.

2. The delayed-action insecticide of claim 1 wherein the anionic fluorochemical surfactant is a potassium perfluoroalkyl sulfonate having a chemical formula of $C_nF_{2n+1}SO_3K$, where n equals 6 or 8.

3. The delayed-action insecticide of claim 1 wherein the anionic fluorochemical surfactant is a potassium perfluoroalkyl cyclohexyl sulfonate having a chemical formula of $C_nF_{2n-1}SO_3K$, where n equals 7 or 8.

4. The delayed-action insecticide of claim 1 wherein the anionic fluorochemical surfactant is dissolved in a solvent which consists of a member selected from the group consisting of acetone and methanol.

5. The delayed-action insecticide of claim 1 wherein the carrier consists of a member selected from the group consisting of dried yellow corn meal, corn grit, crushed wheat, and cracked wheat.

6. The delayed-action insecticide of claim 1 wherein the insecticide further comprises soybean oil subsequently applied to the carrier as an attractant.

7. The delayed-action insecticide of claim 1 wherein the anionic fluorochemical surfactant has a concentration of 0.05 to 1.0% by weight.

8. The delayed-action insecticide of claim 7 wherein the anionic fluorochemical surfactant concentration is approximately 0.1 to 0.5% by weight.

9. The delayed-action insecticide of claim 6 wherein the anionic fluorochemical surfactant has a concentration of 0.3 to 0.5% by weight, the carrier has a concentration of approximately 9.47 to 94.5% by weight, and the soybean oil has a concentration of approximately 5.0% by weight.

10. The delayed-action insecticide of claim 2 wherein the anionic fluorochemical surfactant has a concentration of 0.05 to 1.0% by weight.

11. The delayed-action insecticide of claim 10 wherein the anionic fluorochemical surfactant concentration is approximately 0.1 to 0.5% by weight.

12. A delayed-action insecticide comprising an insecticidal vegetable oil insoluble anionic fluorochemical surfactant and a carrier in the form of deployable nonliquid edible food to form a toxic bait, produced by a method comprising the steps of:

dissolving the anionic fluorochemical surfactant in a solvent;

applying a sufficient amount of the surfactant/solvent solution to the carrier to provide an insecticidal concentration, thereby moistening the carrier; and evaporating the solvent from the carrier.

13. The delayed-action insecticide of claim 12 wherein the method for producing the delayed-action insecticide further comprises the step of subsequently applying soybean oil to the carrier as an attractant.

* * * * *